United States Patent [19]

Michels

[11] Patent Number: 4,822,495

[45] Date of Patent: Apr. 18, 1989

[54] CELL BLOCK COLLECTION METHOD AND APPARATUS

[75] Inventor: Ruth Y. Michels, Clifton, Colo.

[73] Assignee: St. Mary's Hospital and Medical Center, Grand Junction, Colo.

[21] Appl. No.: 70,410

[22] Filed: Jul. 7, 1987

[51] Int. Cl.⁴ .................... B01D 45/12; B65D 39/00
[52] U.S. Cl. .................................. 210/781; 210/238; 210/514; 210/789; 220/1.6; 220/20.5; 422/101; 436/177; 436/178; 494/20; 494/36; 494/37
[58] Field of Search ................ 435/30, 284, 285, 292, 435/293, 294, 296, 299, 311, 313; 220/1 C, 20.5, 306, 307; 422/101, 86, 88; 436/177, 178; 494/36, 37, 16, 20; 210/237, 238, 516, 518, 782, 789, 513, 514, 781, 787

[56] References Cited

U.S. PATENT DOCUMENTS

| | | | |
|---|---|---|---|
| Re. 28,165 | 9/1974 | McCormick | 220/367 |
| 4,034,884 | 7/1977 | White | 220/355 |
| 4,220,252 | 9/1980 | Beall et al. | 220/266 |
| 4,417,981 | 11/1983 | Nugent | 210/516 |
| 4,421,246 | 12/1983 | Schultz et al. | 206/205 |

*Primary Examiner*—W. Gary Jones
*Attorney, Agent, or Firm*—Holme Roberts & Owen

[57] ABSTRACT

A cassette has a foraminous lower portion which is shaped to receive a button or pellet of agar and is capable of being placed in the bottom of a fluid container for use in a centrifuge. After the cassette portion is placed in the container, a fluid containing cells is poured in the container which is then centrifuged causing the cells to adhere to the agar. The fluid is then poured out, the cassette lower portion removed from the container and an upper foraminous cassette portion is used to cover the lower portion and enclose the agar with adhered cells.

10 Claims, 2 Drawing Sheets

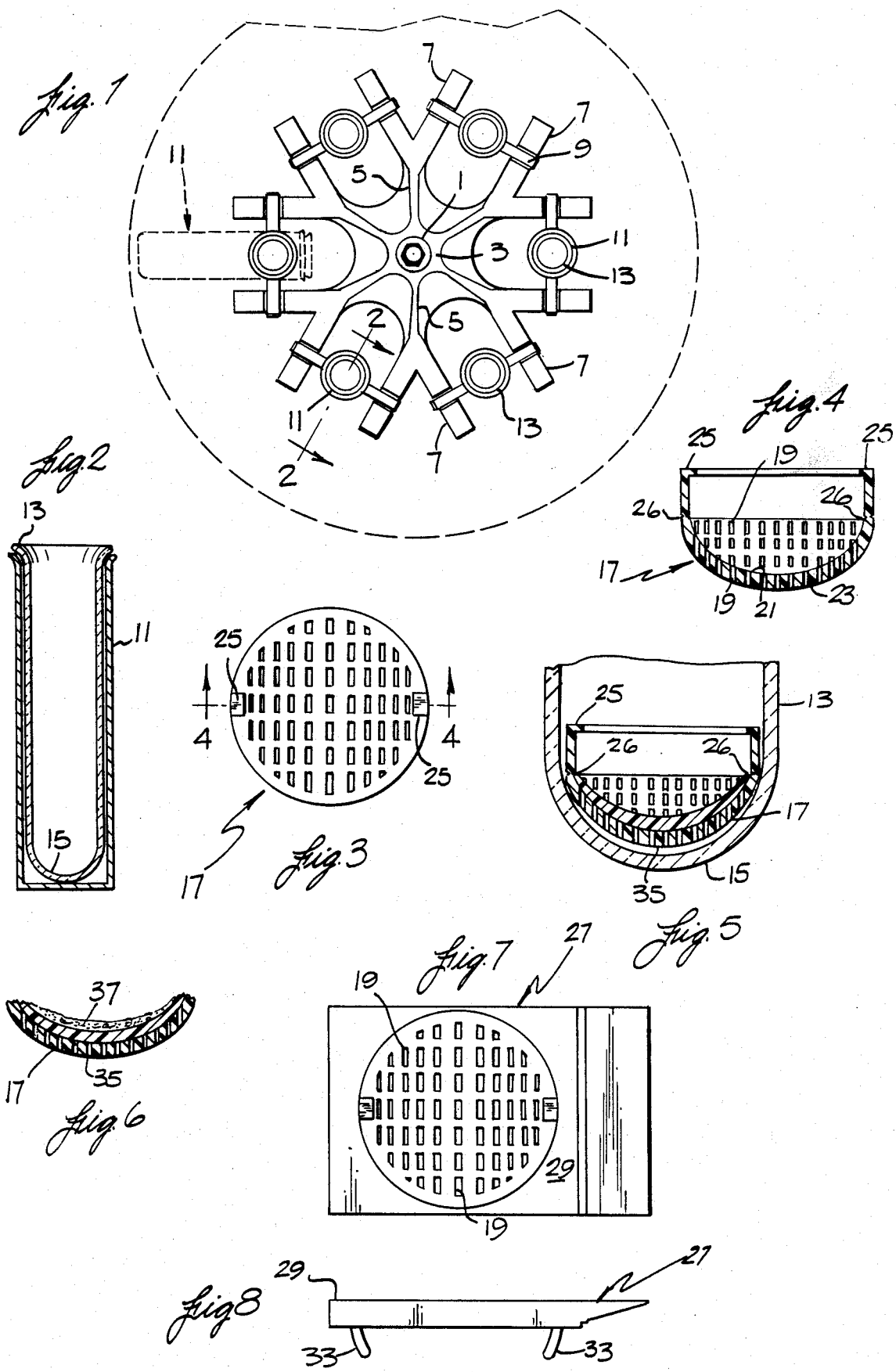

CELL BLOCK COLLECTION METHOD AND APPARATUS

This invention relates primarily to a method and a device for separating animal cells, tissue and the like from fluids, and collecting such particles in a state suitable for use in microscopic examination procedures. The invention is particularly useful in processing so called "fine needle aspiration biopsy aspirates" or other small anatomical biopsies, but it will be apparent that the invention has application to procedures for separating and collecting other particulate substances from fluid in which they are suspended. The device of this invention is a so-called "cassette" of the general types disclosed in U.S. Pat. Nos. Re 28,165; 4,034,884; 4,220,252 and 4,421,246.

BACKGROUND AND SUMMARY OF THE INVENTION

Microscopic examination of animal cells typically involves first taking a sample of body fluid consisting of a relatively large quantity of fluid and very few cells. To facilitate examination of the cells it is necessary to remove them from the fluid and collect them in concentrated form.

Typically cells are separated from the fluid by placing the cell-containing fluid in a glass or plastic container similar to a common test tube, and then placing the container in a receptacle of a centrifuge which when rotated causes the cells to move to the outer end or bottom of the container. The fluid is then decanted away leaving a concentration of cells and some fluid in the bottom of the container. Then a small amount of a mucilaginous substance, such as agar, is placed in the container and the mixture of cells and the substance is again centrifuged. This second centrifuging results in a "button" of the substance with a concentration of cells in its bottom surface. The button is then removed from the container and the excess substance is carefully trimmed away. The trimmed button is mounted in a paraffin block which is then sliced in cell-thick sections suitable for mounting on a microscope slide.

Removing the button from the container is a delicate procedure. It is normally done with a wooden applicator and quite often the button is broken up. The button, or what is then left of it, is placed in an enclosure called a "cassette" consisting of rectangular upper and lower parts having slots or holes in their major faces. The cassette containing the trimmed button is then soaked in an appropriate solution to prepare the trimmed button for mounting in the paraffin block.

There are several distinct disadvantages to this prior art procedure. One disadvantage is the necessity for decanting the fluid while the cells are still suspended in the lower levels of the fluid resulting in the possibility of some cells being lost or the uniformity of the concentration of the cells being diminished during the decanting. Another disadvantage is the necessity for centrifuging twice. Another is having the cells on the bottom of the button with no means for removing the portion containing the cells without danger of disruption of the button.

This invention overcomes these disadvantages by using a lower cassette portion which generally can be placed in a fixed position adjacent to the bottom of the fluid container and which has upwardly extending projections which facilitate its removal from the container. The inner cavity of this lower part of the cassette is shaped to receive a button of a mucilaginous substance. The lower cassette part with the button placed in its cavity is first fitted into the bottom of the container and then the body fluid is poured into the container. During centrifuging the cells adhere to the top surface of the button permitting the fluid then to be easily poured away without disturbing the cells. The lower cassette part holding the button and adhered cells is then removed by means of the projections which are then detached. The upper cassette part is then attached to the lower cassette part and the normal procedures of soaking etc. are followed.

The benefits of the present invention thus lie primarily in totally eliminating the disadvantages of the prior art devices and procedures described above. Other benefits and advantages will become apparent to those skilled in the art from the following description of presently preferred embodiments of the invention and from the accompanying drawings.

DESCRIPTION OF THE DRAWINGS

FIG. 1 is an illustration of portions of a centrifuge.

FIG. 2 is a sectional view on the line 2—2 at the bottom of FIG. 1.

FIG. 3 is a plan view of the lower part of a cassette for use in forming a cell block.

FIG. 4 is a sectional view of the device of FIG. 3.

FIG. 5 is a sectional view of a fluid container in which the device of FIGS. 3 and 4 has been placed in the fluid container with mucilaginous material on the top surface of the device of FIGS. 3 and 4.

FIG. 6 is a sectional view of a portion of FIG. 5 after centrifuging.

FIG. 7 is a plan view of the upper part of a cassette.

FIG. 8 is a side view of FIG. 7.

DESCRIPTION OF PREFERRED EMBODIMENTS

Figure 9:
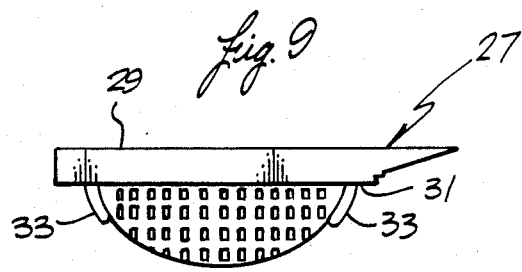
FIG. 9 is a side view of the lower cassette part illustrated in FIG. 6, covered by and attached to the upper cassette part of FIGS. 7 and 8.

Referring to FIG. 1 there is shown a portion of a centrifuge device including a hub 1 adapted to fit over a rotable drive shaft, not shown. To hub 1 a base 3 is connected, the base having a number of outwardly directed arms 5 at the outer end of each of which are two parallel spaced portions 7. The parts 7 each are constructed to hold pivot pins 9 supporting a receptacle 11 for holding a fluid container 13. As illustrated by the dotted lines at the top of FIG. 1 when the centrifuge is rotated around the axis of the hub 1 the receptacles 11 swing upwardly to or toward a horizontal position so that any fluid in the fluid container 13 is subjected to centrifugal force acting in a direction toward the outer end or bottom 15 (see FIG. 2) of the fluid containers. While the method of the present invention can be utilized with any standard centrifuge of the general type shown and the device of the present invention can be adapted to a variety of shapes for the receptacles 11 and fluid containers 13, the simplest construction is for the receptacles 11 to be cylindrical in shape and constructed of metal and for the fluid container 13 to be a standard glass or plastic "test" tube with a cylindrical body and a rounded bottom 15.

Figure 11:
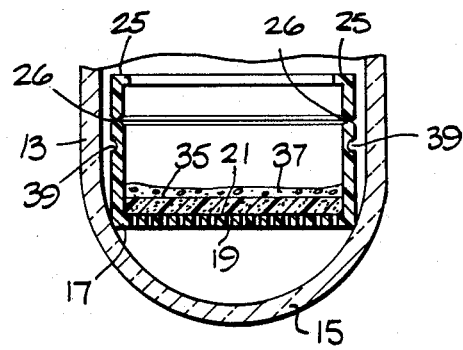
FIG. 11 is a sectional view similar to FIG. 5 showing a further embodiment of the invention.

The device or cassette of the present invention is illustrated in FIGS. 3–9. The device includes a lower part 17 which is shown in a dish-shaped configuration conforming to the shape of the bottom 15 of the fluid container 13. It is not necessary, however, that lower part 17 so conform to the shape of the bottom 15 so long as it provides an upwardly opening (inwardly during centrifuging) cavity suitable for receiving a button of agar or other mucilaginous substance. As illustrated in FIG. 11 the part 17 can be generally cylindrical in shape with a flat bottom wall and dimensioned to fit snugly against the lower, inner wall of tube 13.

As shown in FIGS. 3 and 4 the lower part is provided with a multiplicity of slots 19 extending through from its upper surface 21 to its lower surface 23. While slots are shown, openings of any type which will permit passage of liquids will suffice and hence lower part 17 need only be foraminous and the shape of the openings is not critical. At convenient locations on the rim of lower part 17 there are provided upwardly projecting ears 25 to facilitate handling of part 17. The ears 25 are preferably detachable or removable and in the cassette construction shown in the drawings must be removable. In the drawings indentations 26 are shown in the ears 25 where they join the rim of part 17 to facilitate breaking off the ears.

Figure 10:
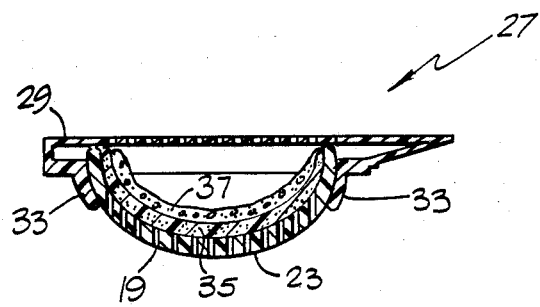
FIG. 10 is a sectional view of the assembled cassette containing the mucilaginous button with adhered cell layer.

The upper part 27 of the cassette of this invention is shown in FIG. 7 as being generally rectangular in plan view. It is provided with slots 19 extending through from its upper surface 29 to its lower surface 31 in an area generally of the same extent in plan view as the slotted area in lower part 17. This area of upper part 27 like the corresponding area of lower part 17 need only be foraminous. Projecting downwardly from the lower surface 31 of upper part 27 are lugs 33 curving inwardly and configured and biased to permit slipping upper part 27 over lower part 17 with the lugs holding the two parts together as shown in FIGS. 9 and 10. The upper part 29 need not be rectangular but making it of the general configuration shown provides surface area for attachment of labels.

The upper and lower cassette parts 27 and 17 are preferably molded from a suitable plastic or resinous material, but in the embodiment of FIG. 11 the material must be of sufficient strength to prevent collapse of lower cassette part 17 during centrifuging.

In carrying out the method of this invention utilizing the cassette shown in the drawings, a button 35 of agar or other mucilaginous material is placed on the upper surface 21 of lower part 17 which is then placed in the bottom 15 of the fluid container 13, as illustrated in FIGS. 5 and 11. Fluid containing the particles to be collected (animal cells, tissue, etc.) is then placed in fluid container 13 which is placed in centrifuge receptacle 11 as illustrated in FIG. 2. The fluid is centrifuged causing suspended particles to move toward and become adhered to the upper (inner during centrifuging) surface of mucilaginous button 35 in a layer 37 illustrated in FIGS. 6, 10 and 11. Container 13 is removed from the centrifuge, the fluid is removed and the lower part 17 is lifted out of the container 13 by pulling upwardly on ears 25, thus avoiding contact with button 35 and layer 37. Ears 25 are then removed from lower part 17 and upper part 27 is slid over lower part 17 with lugs 33 holding the two parts assembled together. The assembled cassette with enclosed button 35 and layer 37 is then processed in the normal manner. In the embodiment of FIG. 11 it may desirable to provide grooves in the outer wall of lower part 17 to receive lugs 33 of upper part 29. When the lower part is cylindrical in shape with a flat bottom wall as shown in FIG. 11, stacking of one cassette atop another is facilitated since the cassette will not tilt as will the construction of FIGS. 9 and 10.

What is claimed is:

1. A method of collecting particles from fluids comprising, placing in the bottom of a fluid container a foraminous member, placing contiguous to the interior surface of the member a mucilaginous substance, placing in the container interiorly of the mucilaginous substance a fluid including the particles, applying a centrifugal force in a direction toward the mucilaginous substance, said mucilaginous substance remaining attached to said foraminous member and being situated in the bottom of the fluid container, and collecting particles from the fluid onto the surface of the substance.

2. The method of claim 1 further comprising removing the member from the receptacle without disturbing the particles.

3. The method of claim 2 further comprising covering the mucilaginous substance with a second foraminous member to form a cassette.

4. A device for collecting particles from fluids comprising means for supporting a layer of a mucilaginous substance such that said layer remains attached to said means during centrifugation of said fluids, said means including a foraminous member having a configuration permitting it to be fitted in the bottom portion of the interior surface of a fluid container of an apparatus for centrifuging fluid, said portion of the interior surface being remote from the axis of the centrifuge during centrifugation, and said member being constructed of a material that allows said member to remain in said bottom portion of the fluid container during centrifugation of said fluids and said layer having a surface forming a means for collecting particles from the fluids onto said surface.

5. The device of claim 4 further comprising removable means for facilitating removal of the member from the fluid container.

6. The device of claim 5 further comprising a second foraminous member capable of being joined to the first member to encase the mucilaginous substance.

7. The device of claim 6 in which the member is round and the second member is rectangular.

8. The device of claim 7 in which the round member is dish-shaped.

9. The device of claim 7 in which the round member has a cylindrical side wall and a flat bottom wall.

10. A cassette for holding a cell block, comprising upper and lower parts each having a major foraminous wall portion; the lower part being round in plan view, being configured to permit its being placed in a fixed position adjacent to the bottom of a centrifuge fluid container, having a cavity arranged to face the upper part when the two parts are attached to each other and having removal means facilitating removal of said lower part from the bottom of a centrifuge fluid container; the upper part being rectangular in plan view; attachment means for attaching the upper part to the lower part with the foraminous wall portion of the upper part being opposite the cavity in the lower part and; said removal means being removable prior to the attachment of the upper part to the lower part.

* * * * *